(12) United States Patent
Holmberg

(10) Patent No.: US 6,569,841 B1
(45) Date of Patent: May 27, 2003

(54) ION EXCHANGE TUMOR TARGETING (IETT)

(75) Inventor: Anders Holmberg, Uppsala (SE)

(73) Assignee: MAP Medical Technologies OY, Tikkakoski (FI)

( * ) Notice: Subject to any disclaimer, the term of this patent is extended or adjusted under 35 U.S.C. 154(b) by 0 days.

(21) Appl. No.: 09/807,542

(22) PCT Filed: Oct. 12, 1999

(86) PCT No.: PCT/SE99/01837

§ 371 (c)(1),
(2), (4) Date: Oct. 3, 2001

(87) PCT Pub. No.: WO00/21571

PCT Pub. Date: Apr. 20, 2000

(30) Foreign Application Priority Data

Oct. 13, 1998 (SE) ............................................... 9803482

(51) Int. Cl.⁷ ............................................. A61K 31/715
(52) U.S. Cl. ........................................... 514/59; 514/52
(58) Field of Search ............................................ 514/59

(56) References Cited

FOREIGN PATENT DOCUMENTS

WO    WO 90/13289 A1    11/1990

OTHER PUBLICATIONS

Bue et al., Abstract of "The potenial of radiolabeled EGF–dextran conjugates in teh treatment of urinary bladder carcinoma", Cancer, 80, 12 Suppl., 2385–2389, Dec. 1997.*
Drug Delivery, vol. 4, 1997, Yasuhiko Tabata et al., "Electric Charge Influence of Dextran Derivatives on their Tumor Accumulation After Intravenous Injection" pp. 213–221.

* cited by examiner

Primary Examiner—Dwayne C. Jones
(74) Attorney, Agent, or Firm—Browdy and Neimark, P.L.L.C.

(57) ABSTRACT

A compound for local, i.e. intratumoral or intracavitary administration, for targeting tumors comprising dextran, the charge of which has been modified through covalent binding of charged groups, such as charged amino acids. The compound further comprises a functional group for treating or imaging the tumor.

21 Claims, 1 Drawing Sheet

ION EXCHANGE TUMOR TARGETING (IETT)

REFERENCE TO RELATED APPLICATIONS

The present application is the national stage under 35 U.S.C. 371 of international application PCT/SE99/01837, filed Oct. 12, 1999 which designated the United States, and which international application was published under PCT Article 21(2) in the English language.

BACKGROUND OF THE INVENTION

Tumor specific targeting, is an intensive research field within oncology. The rationale is to reduce side effects and increase the drug dose that can be delivered to the cancer patient thus enhancing the therapeutic efficacy.

Examples of such targeting are antibody oriented targeting, i.e. immuno-targeting, and controlled drug delivery systems using various polymers as drug carriers (1, 2, 3, 4, 5, 6).

Tabata et al (11) describes intravenous administration of dextran with negative charges. This gives very low specific accumulation of the dextran to the tumor. The specific accumulation or the target to non-target ratio (ttn-ratio) is never exceeding 10 (shown in FIGS. 8 and 9, page 219).

Syrigos et al (12) describes intravesical administration of radiolabelled tumor-associated monoclonal antibody giving a specific accumulation or target to non-target ratio (ttn-ratio) ranging between 2 and 6.

SUMMARY OF THE INVENTION

This invention relates to compounds that, when administered locally, intratumorally or intracavitarily, show unexpectedly high accumulation to tumors and that can deliver various functional groups, including both therapeutic or imaging agents to these sites, to mediate tumor therapy or imaging.

The inventor has discovered that due to the ionic properties of tumors, polymers with an appropriate charge can be selectively targeted to tumors through electrostatic interactions in an ion exchange like reaction. The charged character of tumors could be explained by tumors having enlarged blood vessel surface, abnormal interstitium, and high content of sialic-acid at the cell surface. All these contain charged, mainly anionic, carbohydrates (sulphated carbohydrates) and proteins (collagen) (7, 8). The selective accumulation is unexpectedly high when administered locally, intratumorally or intracavitarily.

By using these charged groups characteristic for tumors as target, the invention avoids the general limitations of tumor specific targeting, such as low affinities between targeting compound and tumor etc. Targeting tumors with compounds according to the invention avoids the problem of tumor heterogeneity, i.e. the limitation of antibody-based cancer therapies that target only a single type of tumor cells in a tumor containing multiple cell types. Further more, tumor therapy or imaging using compounds according to present invention do not require an initial pre-targeting step, as many prior art methods do.

The compounds according to the invention show, when administered locally, intratumorally or intracavitarily, unexpectedly high affinities for tumors, i.e. they have an unexpectedly high target to non-target (ttn) ratio (see Example 2). The charge of the compounds can be adapted to the charge of the tumor to be treated, thereby increasing the target to non-target ratio of the compound to the tumor. When looking at the general properties of solid tumors, it seems probable that the principle of the invention, i.e. selective accumulation in tumor tissue through interactions between the charges of the tumor and the polymer, is functional in most human solid tumors.

In preferred embodiments, the compounds of the invention comprise a targeting compound, which is a charged polymer that binds selectively to the tumor through electrostatic interactions. The targeting compound is modified to include a functional group, which may be part of the polymer or attached to the polymer as a tag. Where the compound is to be used therapeutically the functional group is a toxin, a drug, a radioactive molecule or a precursor thereof. Where the compound is to be used for tumor imaging rather than therapy, the functional group may also be a detectable label, such as a radioactive molecule.

DETAILED DESCRIPTION OF THE INVENTION

The compounds according to the invention are for local, i.e. intracavitary or intratumoral administration. Examples of tumors suitable for such administration are tumors growing in body-cavities such as urinary bladder tumors, ovarian tumors, certain brain tumors, and for intratumoral administration, pancreatic tumors, and head and neck tumors. When the compounds according to the invention are administered locally, intratumorally or intracavitarily the specific accumulation or ttn-ratio ranges between 700 and 2050, which far exceeds specific accumulation when administered according to prior art.

The compounds according to the invention comprise a charged polymer, which causes the targeting, and a functional group, which causes the therapy or imaging.

In preferred embodiments the targeting polymer of the compound according to the invention is a poly-alcohol, such as dextran. When using dextran, a preferred molecular weight is between $10^3$–$10^6$ Dalton. In a preferred embodiment the charged side groups of the polymer are amino acids having charged side chains, or derivatives thereof, such as ornithine, lysine, arginine, histidine, glutamic acid, aspartic acid etc. The amino acids are coupled to dextran by activating the hydroxyl groups of dextran through partial oxidation to aldehydes which react with the free amino groups of the amino acids. This procedure is described in Foster, R L. 1975 (10). An example of a resulting compound (lysine-dextran) according to the invention is shown in FIG. 1. In a preferred embodiment an amino acid is coupled to between 15–30% of the glucose residues of dextran.

The resulting charge of the compound can be positive, negative or neutral depending of the requirements, i.e. the electrostatic properties of the type of tumor to be targeted.

Examples of the functional group of the compound according to the invention include drugs (e.g. antibiotics, anti-virals, anti-fungals), toxins (e.g. ricin), radio-nuclides (e.g. Cu-64, Cu-67, Sr-89, Y-90, Tc-99m, I-131, Sm-153, Ho-166, Re-186, Re-188, Bi-212), hormone antagonists (e.g. tamoxifen), heavy metal complexes (e.g. cisplatin), oligo-nucleotides (e.g. antisense oligo-nucleotides), chemo-therapeutic nucleotides, peptides, non-specific (non-antibody) proteins, boron containing compounds (e.g. carborane), photodynamic agents (e.g. rhodamine), ene-diynes (e.g. calichesmicins), and transcriptions based pharmaceuticals.

Coupling of the functional group could be done either directly to the polymer or through a bifunctional chelate, such as an aminated radio-metal chelate. Direct coupling of the functional group to the poly-alcohol could be achieved in the same manner as the charged side-groups are coupled to the poly-alcohol. The binding of the functional group must not allow release of the functional group in vivo.

The compounds according to the invention can be administered alone, or in conjunction with a pharmaceutically acceptable carrier.

EXAMPLES

This invention will now be described in greater detail by reference to the following non-limiting examples in which:

Example 1

Figure 1:
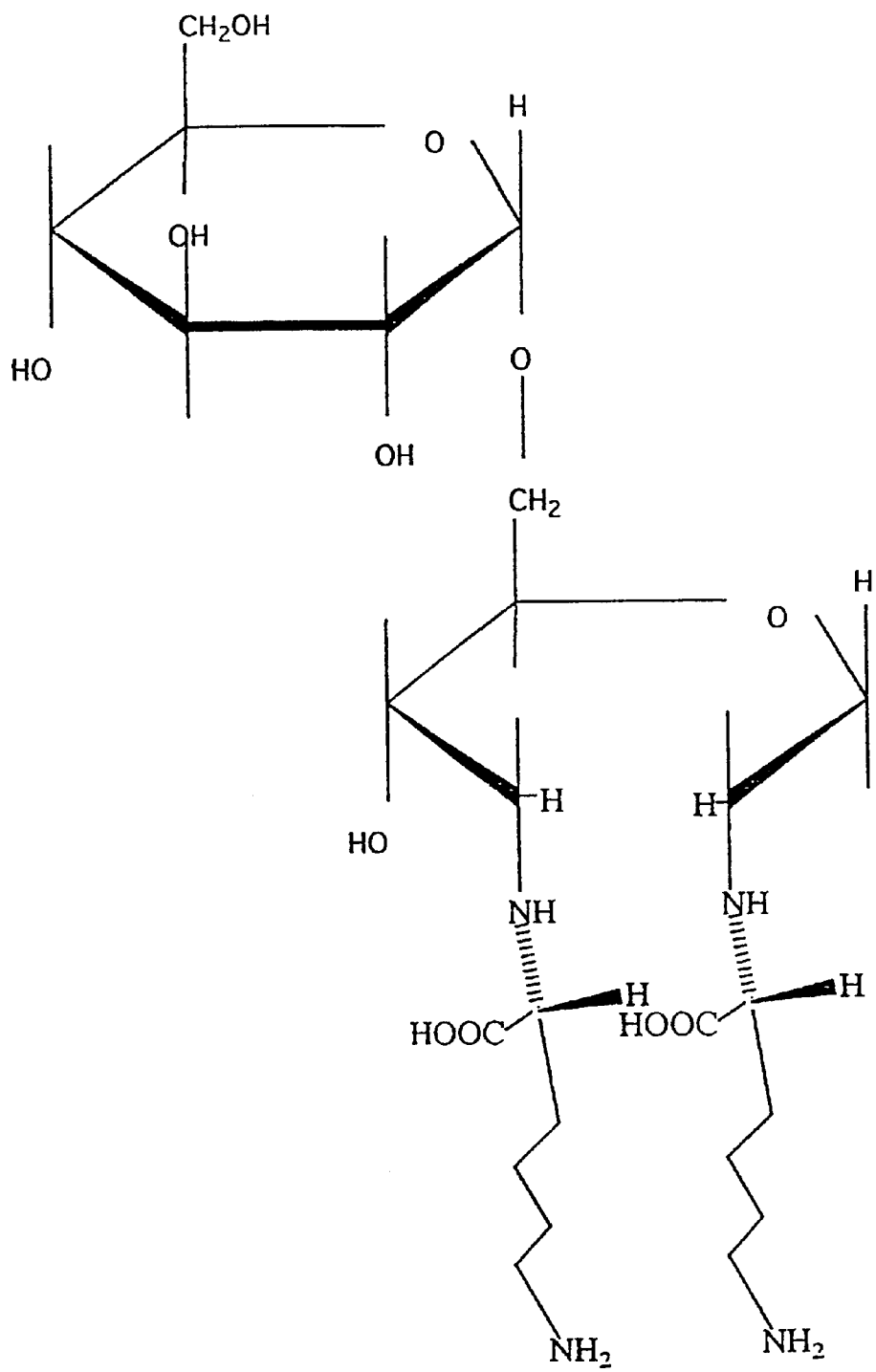
FIG. 1 shows an example of a compound according to the invention wherein the amino acid lysine is coupled to dextran, according to the invention.

Synthesis of Tc-99m-lysine-dextran according to the invention. Activation of the hydroxyl groups of dextran. 20 mg of dextran (mean mw 40000 Dalton, Pharmacia-Amersham Biotech, Sweden) is mixed with 12 mg sodium periodate in a total volume of 1mL 0.15 M sodium acetate, pH 5.5 and incubated during stirring at room-temperature for 5 h. The polymer is then purified on a disposable Sephadex®-G25 (Pharmacia-Amersham Biotech, Sweden) gel filtration column.

Coupling of lysine to activated dextran. 20 mg of the activated dextran is mixed with a large molar excess of lysine (28 mg lysine), in 2.1 mL of 0.1M NaHCO$_3$ and 4mg of sodium cyanoborohydride is added. The mixture is incubated during stirring at room temperature for ~15 h. After incubation the compound is purified on a PD 10 column and the buffer is exchanged to 0.1M sodium acetate. This results in the coupling of a lysine to approximately 15–30% of the glucose residues of dextran.

Labeling of lysine-dextran with technetium (Tc-99m). Labeling of lysine-dextran with Tc-99m is performed according to the method of Henze et al. (9), i.e., 50 µg SnCl$_2$ (10 µL of konc. 5 g/L, in 99% ethanol) is added to 50 µg lysine-dextran in 1 mL 0.1M sodium acetate. Then ~100 MBq sodium pertechnetate (~100 µL) is added and the reaction mixture is incubated for 15 minutes at room temperature. The solution is purified on a Sephadex®-G25 PD10 column (Pharmacia-Amersham Biotech, Sweden), sterile filtrated, and dilute in 150–200 ml saline. After labeling the compound should be used directly. All solutions above are degassed. The resulting Tc-99m lysine dextran contained 1 MBq per µg.

Example 2

This example serves to demonstrate that Tc-99m-lysine dextran according to the invention is selectively accumulated in tumor tissue.

Nine patients having epidermal growth factor positive superficial transitional cell bladder carcinoma were studied. Tc-99m-dextran with different charges and containing the same total amount of radio-activity were instilled in the bladder of these patients. The instilled polymers were Tc-99m-epidermal growth factor (EGF)-dextran, neutral dextran, i.e. Tc-99m-dextran, anionic dextran, i.e. Tc-99m-taurin dextran, and cationic dextran, i.e. Tc-99m-lysine dextran (according to Example 1).

200 mL of the polymers, of the concentration 0.25 µg/mL in saline, were instilled through an urethral catether and kept in the bladder for 30 minutes and were then carefully washed out with approximately 400 mL saline. The patients were then operated on and samples were taken from normal bladder tissue and bladder tumor tissue, respectively. The samples were weighed and counted in gamma counter and the radioactive uptake was calculated as cpm/g tissue. The target to non-target (ttn) ratio was calculated. Results (mean values) are shown in Table 1.

TABLE 1

| polymer | radioactive uptake, ttn | number of patients studied |
|---|---|---|
| Tc-99m-EGF-dextran | 700:1 | 4 |
| Tc-99m-dextran | 90:1 | 1 |
| Tc-99m-taurin dextran | 2:1 | 1 |
| Tc-99m-lysine dextran | 2050:1 | 2 |

The Tc-99m-lysine-dextran according to the invention resulted in the highest tumor uptake of radioactivity, i.e. the highest target to non-target ratio. Tc-99m-EGF-dextran serves as a comparison with prior art techniques, i.e. targeting to tumors by antibodies directed to proteins that normally are over-expressed in tumors. However, the conditions in this study were unfavorable for the interaction between the Tc-99m-EGF-dextran and EGF-receptors expressed by tumors, hence the large ttn ratio was interpreted as charge dependent through charged side groups of Tc-99m-EGF-dextran.

REFERENCES

1. Hurwitz E. Specific and nonspecific macromolecule-drug conjugates for the improvement of cancer chemotherapy. Biopolym. 1983; 22, 557–567.
2. Maeda H, Seymour L W, Miyamoto Y. Conjugates of anti-cancer agents and polymers: Advantages of macromolecular therapeutics in vivo. Bioconj. Chem. 1992; 3, 5, 353–363.
3. Rogers K E, Carr B I, Tökes Z. Cell surface-mediated cytotoxicity of polymer-bound adriamycin against drug-resistant hepatocytes. Cancer Res. 1983; 43, 2741–2748.
4. Schacht E, Vermeersch E et al. Synthyesis and characterization of some modified polysaccarides containing drug moieties. J. Controlled Release. 1985; 2, 245–256.
5. Seymour L W. Passive tumor targeting of soluble macromolecules and drug conjugates. Critical Rev. Therap. Drug Carrier Syst. 1992; 9, 135–187.
6. Sezaki H, Hashida H et al. Macromolecule-drug conjugates in targeted cancer chemotherapy. Biodegradable polymers in controlled drug delivery. Critical Rev. Therap. Drug. Carrier Syst. 1984; 1,1, 1–37.
7. Comper W D and Laurent, T C. Physiological Function of Connective Tissue Polysaccarides. Physiological Reviews 58:255–315, 1978.
8. Grodzinsky A J. Electromechanical and Physiochemical Properties of Connective Tissue. CRC Critical Reviews in Biomedical Engineering 9:133–199.
9. Henze E and Robinson G D. Tc-99m dextran: A new blood-pool labeling agent for radionucllide angiocardiography. J. Nucl. Med. 23:348–353, 1982
10. Foster, R L. Preparation and properties of a soloubble trypsin-dextran conjugate. Expertia 31:772–773, 1975.
11. Tabata et al. Drug Delivery 4:213–221, 1997.
12. Syrigos et al. Acta Oncologia Vol 38, No 3, pp.379–382, 1999

What is claimed is:

1. A method for treating charged tumors by an ion exchange reaction comprising administering to a patient in need thereof an effective amount of a composition comprising dextran having a charge opposite that of said charged tumor, in which the charge of said dextran has been modified by covalent bonding of charged groups.

2. The method according to claim 1 wherein the composition is administered by a method selected from the group consisting of local, intratumoral, and intracavitary.

3. The method according to claim 1 wherein the charged groups are selected from the group consisting of amino acids with charged side chains and derivatives thereof.

4. The method according to claim 3 wherein the amino acids are selected from the group consisting of ornithine, lysine, taurine, arginine, histidine, glutamic acid, and aspartic acid.

5. The method according to claim 1 wherein the charged groups are bound to activated hydroxyl groups of dextran.

6. The method according to claim 1 wherein a charged group is bound to 15–30% of the glucose residues or dextran.

7. The method according to claim 1 wherein the dextran contains functional groups.

8. The method according to claim 7 wherein the functional groups are bound to the activated hydroxyl groups of dextran.

9. The method according to claim 7 wherein the functional groups are selected from the group consisting of radionuclides.

10. The method according to claim 1 wherein the dextran has a molecular weight of $10^3$ to $10^6$ daltons.

11. The method according to claim 1 wherein the composition is localized to the tumor at a target to non-target ratio of at least 600:1.

12. The method according to claim 1 wherein the charge of said dextran is adapted to the charge of the tumor to be treated, thereby increasing the target to non-target ratio of the compound to the tumor.

13. The method according to claim 1 wherein the tumor is a bladder carcinoma tumor.

14. A method for treating charged tumors by an ion exchange reaction comprising
administering to a patient in need thereof an effective amount of a composition comprising dextran,
wherein the charge of the dextran has been modified through covalent bonding of cationic groups and
wherein the charged tumor is an anionic tumor.

15. The method according to claim 14 wherein the composition is administered by a method selected from the group consisting of local, intratumoral, and intracavitary.

16. The method according to claim 14 wherein the charged groups are bound to activated hydroxyl groups of dextran.

17. The method according to claim 14 wherein a charged group is bound to 15–30% of the glucose residues or dextran.

18. The method according to claim 14 wherein the dextran has a molecular weight of $10^3$ to $10^6$ daltons.

19. The method according to claim 14 wherein the composition is localized to the tumor at a target to non-target ratio of at least 600:1.

20. The method according to claim 14 wherein the charge of said dextran is adapted to the charge of the tumor to be treated, thereby increasing the target to non-target ratio of the compound to the tumor.

21. The method according to claim 14 wherein the tumor is a bladder carcinoma tumor.

* * * * *